United States Patent
Chang et al.

(10) Patent No.: US 9,404,773 B2
(45) Date of Patent: Aug. 2, 2016

(54) APPARATUS AND METHOD FOR INSPECTING PIPELINES

(75) Inventors: Hyun Young Chang, Gyeonggi-Do (KR); Dong Wook Kim, Gyeonggi-do (KR); Heung Bae Park, Seoul (KR); Sang Heon Lee, Gyeongsangbuk-do (KR)

(73) Assignee: KEPCO ENGINEERING & CONSTRUTION COMPANY, INC., Gyeongsangbuk-do (KR)

( * ) Notice: Subject to any disclaimer, the term of this patent is extended or adjusted under 35 U.S.C. 154(b) by 376 days.

(21) Appl. No.: 14/131,584

(22) PCT Filed: Jul. 13, 2012

(86) PCT No.: PCT/KR2012/005551
§ 371 (c)(1),
(2), (4) Date: Apr. 2, 2014

(87) PCT Pub. No.: WO2013/009118
PCT Pub. Date: Jan. 17, 2013

(65) Prior Publication Data
US 2014/0338472 A1    Nov. 20, 2014

(30) Foreign Application Priority Data
Jul. 13, 2011 (KR) .................. 10-2011-0069469

(51) Int. Cl.
*G01D 11/30* (2006.01)
*G21C 17/017* (2006.01)
(Continued)

(52) U.S. Cl.
CPC *G01D 11/30* (2013.01); *F17D 5/00* (2013.01); *G01N 21/952* (2013.01); *G21C 17/017* (2013.01)

(58) Field of Classification Search
CPC ........ G01D 11/30; F17D 5/00; G21C 17/017; G01N 21/952
See application file for complete search history.

(56) References Cited

U.S. PATENT DOCUMENTS

| 6,497,159 B1 | 12/2002 | Lavoie |
| 2009/0038398 A1 | 2/2009 | Lavoie |

(Continued)

FOREIGN PATENT DOCUMENTS

| JP | 6096394 B2 | 11/1994 |
| JP | 10-010100 A1 | 1/1998 |

(Continued)

OTHER PUBLICATIONS

Notice of Allowance dated Jan. 29, 2013 of Priority Korean Patent Application No. 10-2011-0069469 (6 pages).

*Primary Examiner* — Hezron E Williams
*Assistant Examiner* — David Z Huang
(74) *Attorney, Agent, or Firm* — Schwabe, Williamson & Wyatt P.C.

(57) ABSTRACT

Apparatus and method for inspecting pipeline are provided. The pipeline inspecting apparatus moving along an external circumferential surface of a pipeline to inspect the pipeline, includes: a main frame having an arc shape having an opened portion to surround the pipeline; a main movement unit that is movably installed on the main frame, wherein the main movement unit is movably installed along a length direction of the pipeline while being in contact with the external circumferential surface of the pipeline; an auxiliary frame that has an arc shape having an opened portion to surround the pipeline and is separated from the main frame to face the main frame; an auxiliary frame adjusting unit that movably connects the auxiliary frame to the main movement unit in a circumferential direction of the pipeline; and a sensor adjusting unit that is fixed to the auxiliary frame, wherein a sensor for inspecting a state of the pipeline is installed.

13 Claims, 6 Drawing Sheets

(51) Int. Cl.
*G01N 21/952* (2006.01)
*F17D 5/00* (2006.01)

(56) References Cited

U.S. PATENT DOCUMENTS

2010/0150296 A1* 6/2010 Togasawa ............ G21C 17/017
376/260

2011/0168900 A1* 7/2011 Dobbs .................... G01B 15/02
250/360.1

FOREIGN PATENT DOCUMENTS

| | | |
|---|---|---|
| JP | 2012-021891 A | 2/2012 |
| KR | 10-0367823 B1 | 12/2002 |
| KR | 10-2005-0121779 A | 12/2005 |

* cited by examiner

APPARATUS AND METHOD FOR INSPECTING PIPELINES

RELATED APPLICATIONS

This application is a U.S. National Phase filing under 35 U.S.C. 371 of International Application Number PCT/KR2012/005551 filed Jul. 13, 2012 and claims priority from Korean Patent Application No. 10-2011-0069469, filed on Jul. 13, 2011, in the Korean Intellectual Property Office, the disclosures of which are incorporated herein in their entirety by reference.

TECHNICAL FIELD

The present invention relates to apparatus and method for inspecting pipelines.

BACKGROUND ART

In industrial facilities such as nuclear power plants, pipelines to be used as flow passages of various fluids flowing in an operation of the industrial facilities are installed. The pipelines have various shapes such as curved surfaces and pipe bends and various sizes. The pipelines need to be inspected in order to provide a smooth flow of fluids and to prevent leakage of the fluids.

When inspection of pipelines is performed while operating the industrial facilities, due to safety problems, for example, an automated inspection apparatus is used for inspection.

In general, the inspection apparatus has a structure in which a probe having a structure, in which a single-axis robot arm and an electromagnetic wheel are coupled to a body of the probe, is used in automatic inspection, and the probe moves along a guide rack that is mounted in advance in a circumferential direction of a pipeline to perform inspection of the pipeline. The guide rack is installed on an external circumferential surface of the pipeline before inspection using the inspection apparatus is performed.

In addition, the inspection apparatus is controlled such that the probe moves in scan and index directions that are input in advance, and here, the scan direction is an axial direction of the pipeline, and the index direction is a circumferential direction of the pipeline.

Meanwhile, since an operator has to install the guide rack on the external circumferential surface of the pipeline in advance, it may be difficult to install the guide rack while the industrial facilities are in operation. Moreover, the guide rack has to be removed from the pipeline after inspection is completed.

Also, it is difficult to install the guide rack in industrial facilities, which are substantially difficult for operators to access, such as pipelines of nuclear power plants.

In addition, if a support structure for supporting the pipelines interferes with movement of the inspection apparatus, separation and reinstallation of the inspection apparatus are to be repeatedly performed, and thus inspection may not be performed easily.

DISCLOSURE OF THE INVENTION

Technical Problem

The present invention provides an apparatus for inspecting pipelines, which is easily installed and improves inspection efficiency.

Technical Solution

According to an aspect of the present invention, there is provided a pipeline inspecting apparatus moving along an external circumferential surface of a pipeline to inspect the pipeline, the apparatus comprising: a main frame having an arc shape having an opened portion to surround the pipeline; a main movement unit that is movably installed on the main frame, wherein the main movement unit is movably installed along a length direction of the pipeline while being in contact with the external circumferential surface of the pipeline; an auxiliary frame that has an arc shape having an opened portion to surround the pipeline and is separated from the main frame to face the main frame; an auxiliary frame adjusting unit that movably connects the auxiliary frame to the main movement unit in a circumferential direction of the pipeline; and a sensor adjusting unit that is fixed to the auxiliary frame, wherein a sensor for inspecting a state of the pipeline is installed.

The main movement unit may comprise a center side main movement unit installed in a center portion of the main frame; and a pair of end side main movement units that are spaced apart from each other with respect to the center side main movement unit, wherein the end side main movement units are movably installed on the main frame in the circumferential direction of the pipeline, wherein the center side main movement unit and the end side main movement units respectively contact three points of the external circumferential surface of the pipeline that are spaced apart at predetermined angles with respect to a center of the pipeline.

The center side main movement unit and the end side main movement units each may comprise a movement bracket that is slidably connected along the main frame in the circumferential direction of the pipeline; a driving unit that provides a driving force for rotating the movement bracket; an extension unit that is extended from the movement bracket toward the pipeline; and a movement wheel that is rotatably connected to the extension unit around a rotation axis that crosses a length direction of the pipeline, and selectively contacts the external circumferential surface of the pipeline.

The center side main movement unit and the end side main movement units may comprise an auxiliary wheel that is disposed adjacent to the movement wheel, and is rotatably installed in the same direction as the movement wheel.

The extension unit may be length-variable such that a distance between the movement wheel and the movement bracket is adjustable.

The auxiliary frame adjusting unit may comprise a center side adjusting unit that is disposed in a center portion of the main frame; and a pair of end side adjusting units that are spaced apart from each other with respect to the center side main movement unit, wherein one ends of the center side adjusting unit and the end side adjusting units are connected to the main movement unit and another ends of the center side adjusting unit and the end side adjusting units are connected to the auxiliary frame so as to rotatably connect the auxiliary frame with respect to the main frame in the circumferential direction of the pipeline.

The center side main movement unit and the end side main movement units each may comprise a first adjustment frame, whose one end is connected to the main movement unit, wherein the first adjustment frame is extended in the length direction of the pipeline; a second adjustment frame that is extended in a direction that crosses the direction in which the first adjustment frame is extended, wherein one end of the second adjustment frame is connected to the first adjustment frame, and the second adjustment frame is movable in the extension direction of the first adjustment frame; and a first driving unit, whose one end is movably connected to the second adjustment frame in the extension direction of the second adjustment frame, wherein the first driving unit provides a driving force to rotate the auxiliary frame in the circumferential direction of the pipeline.

The center side adjusting unit and the end side adjusting units each may comprise a second driving unit that provides a driving force that moves the second adjustment frame with respect to the first adjustment frame.

The sensor adjusting unit may comprise a first guide rail, whose one end is fixed to a center of the auxiliary frame and which extends in a direction perpendicular to the external circumferential surface of the pipeline; and a sensor movement unit that is movably installed in the extension direction of the first guide rail, wherein the sensor is installed in the movement unit.

The pipeline inspecting apparatus may further comprise a pair of pipeline supporting units, wherein one ends of the pipeline supporting units are fixed to the end portions of the main frame and another ends of the pipeline supporting units are selectively contacted to the external circumferential surface of the pipeline so as to fix the main frame with respect to the pipeline.

The pipeline supporting units may comprise a fixing unit that is fixed to the end portions of the main frame; an connection unit that is extended toward the pipeline while one end of the connection unit is connected to the fixing unit, and an extension length of the connection unit is variable; and a contact unit that is installed at another end of the connection unit and selectively contacts the external circumferential surface of the pipeline.

According to an another aspect of the present invention, there is provided a pipeline inspecting method using the pipeline inspecting apparatus, the method comprising installing the pipeline inspecting apparatus to a pipeline such that each movement wheel of a plurality of main movement units contacts an external circumferential surface of the pipeline; moving the pipeline inspecting apparatus in a length direction of the pipeline; and inspecting a state of the pipeline by rotating an auxiliary frame of the pipeline inspecting apparatus in a circumferential direction of the pipeline while the plurality of main movement units of the pipeline inspecting apparatus are stopped.

The pipeline inspecting method may further comprising avoiding interference due to an obstacle when movement of the pipeline inspecting apparatus is interfered by the obstacle during the moving, by rotating a main frame and the main movement units of the pipeline inspecting apparatus, wherein the avoiding comprises: fixing the main frame to the pipeline by using a pair of pipeline supporting units installed at end portions of the main frame; lifting a movement wheel of the main movement units contacting the pipeline while the main frame is fixed to the pipeline, thereby release the contact between the movement wheel and the pipeline; moving the main movement unit along the main frame in a circumferential direction of the pipeline after lifting up the movement wheel; contacting the movement wheel of the main movement unit to the external circumferential surface of the pipeline after the main movement units are moved in the circumferential direction of the pipeline; and releasing the fixation of the pipeline supporting units that fix the main frame to the pipeline.

Advantageous Effects

According to the embodiments of the present invention, a pipeline inspecting apparatus may be easily installed on a pipeline, and even when the pipeline has a form of a pipe bend that is curved at a predetermined angle, inspection with respect to the pipeline may be performed reliably.

In addition, as a main frame of the pipeline inspecting apparatus has an opened portion, an obstacle such as a support of the pipeline may be avoided when the pipeline inspecting apparatus moves in a length direction of the pipeline.

BEST MODE FOR CARRYING OUT THE INVENTION

Hereinafter, preferred embodiments of the present invention will be described in detail with accompanied drawings.

Figure 1:
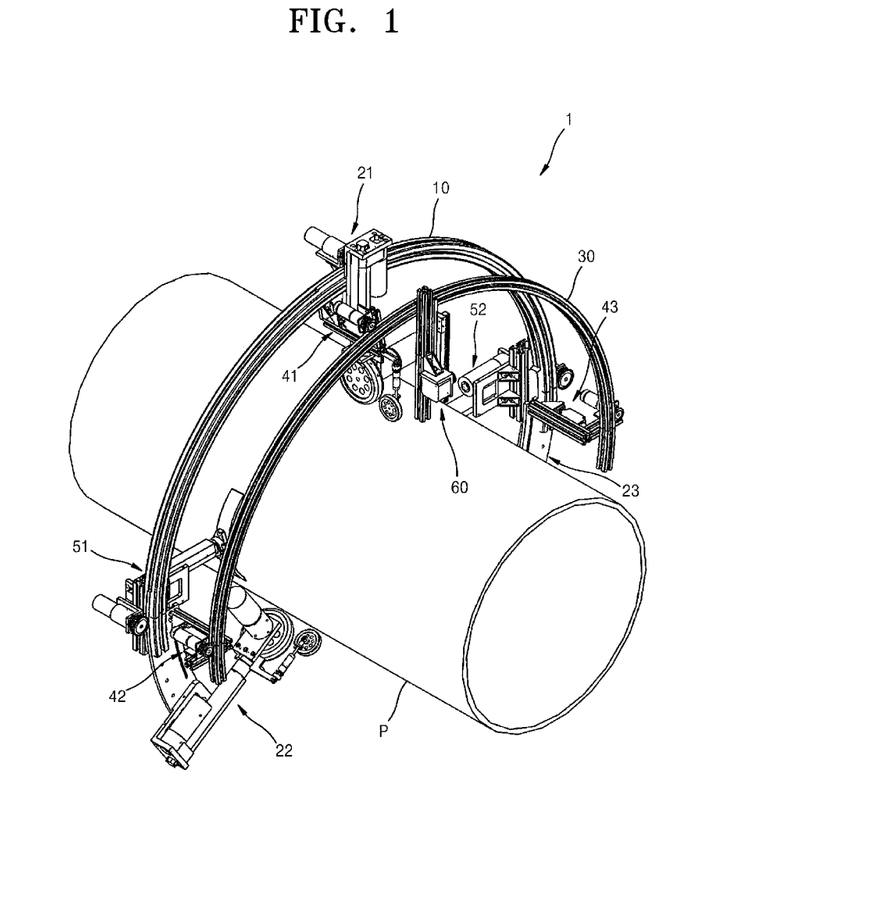
FIG. 1 is a perspective view of a pipeline inspecting apparatus according to an embodiment of the present invention.
Figure 2:
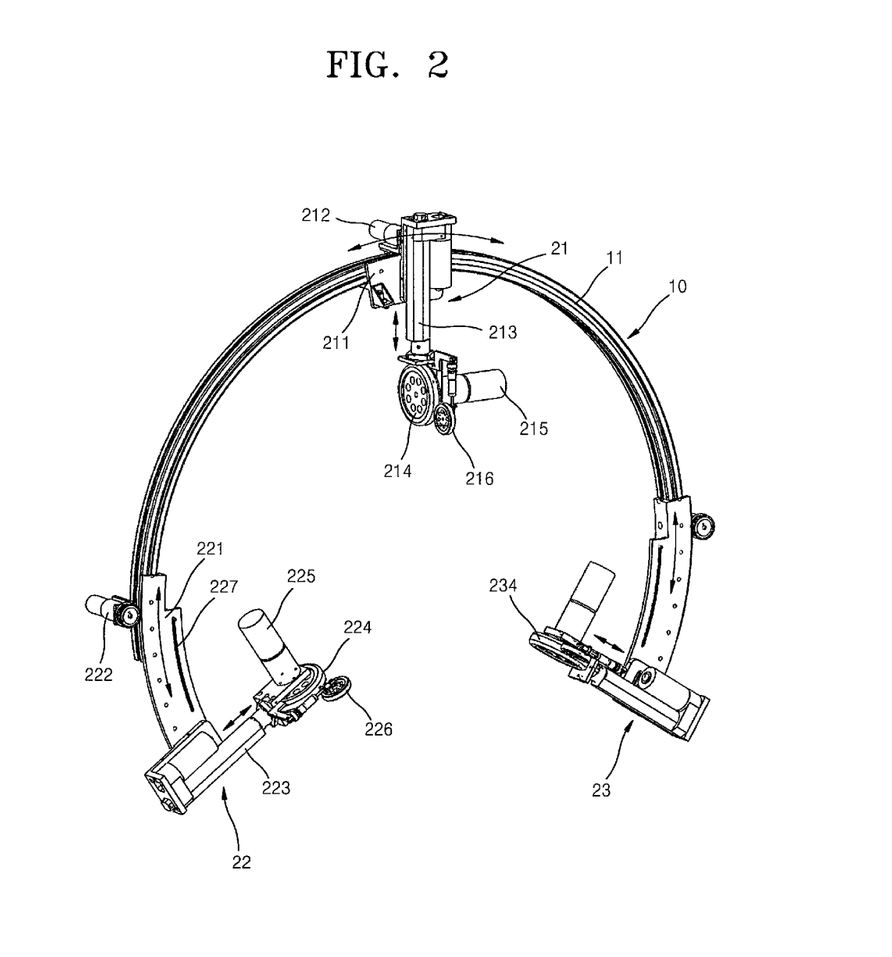
FIG. 2 is a schematic view illustrating a main frame and main movement units of the pipeline inspecting apparatus of FIG. 1.
Figure 3:
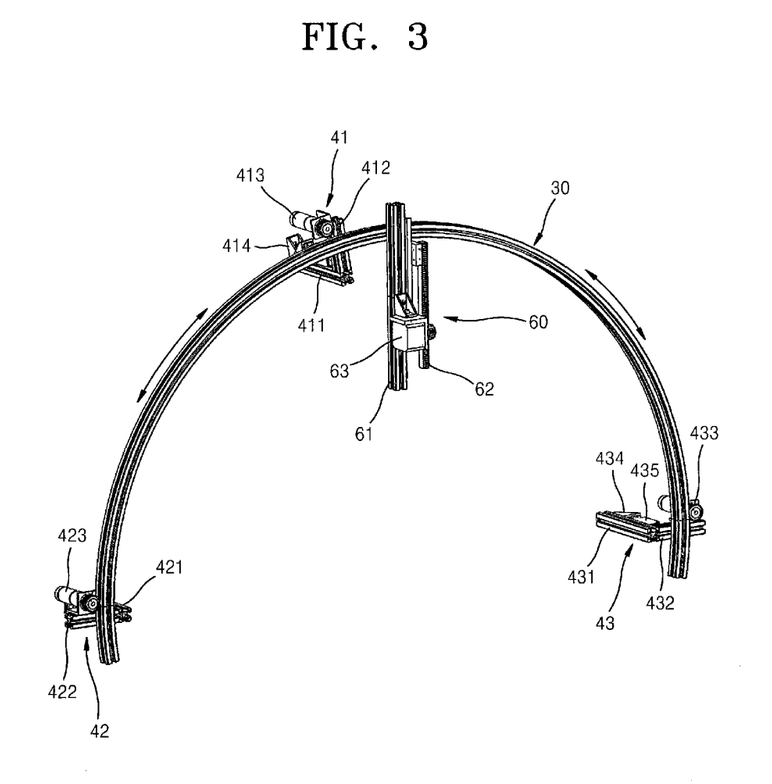
FIG. 3 is a schematic view of an auxiliary frame, an auxiliary frame adjusting unit, and a sensor adjusting unit of the pipeline inspecting apparatus of FIG. 1.
Figure 4:
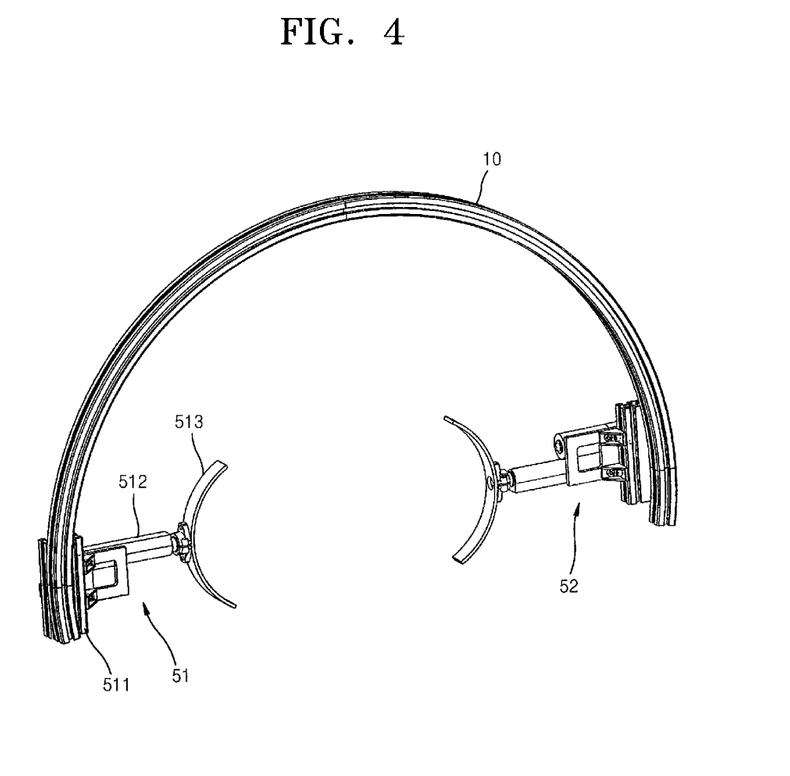
FIG. 4 illustrates the main frame and pipeline supporting units of FIG. 1.

FIG. 1 is a perspective view of a pipeline inspecting apparatus 1 according to an embodiment of the present invention. FIG. 2 is a schematic view illustrating a main frame and main movement units of the pipeline inspecting apparatus of FIG. 1. FIG. 3 is a schematic view of an auxiliary frame, an auxiliary frame adjusting unit, and a sensor adjusting unit of the pipeline inspecting apparatus of FIG. 1. FIG. 4 illustrates the main frame and pipeline supporting units of FIG. 1.

Referring to FIGS. 1 through 4, the pipeline inspecting apparatus 1 is formed to be installable on a pipeline P without an additional guide rail. In addition, instead of operating the pipeline inspecting apparatus 1 where the pipeline inspecting apparatus 1 is installed, an operator may perform inspection safely by moving the pipeline inspecting apparatus 1 in a length direction or a circumferential direction of the pipeline P in a place that is away from the above place where the pipeline inspecting apparatus 1 is installed.

The pipeline inspecting apparatus 1 includes a main frame 10, main movement units 21, 22, and 23, an auxiliary frame 30, auxiliary frame adjusting units 41, 42, and 43, a sensor adjusting unit 60, and pipeline supporting units 51 and 52.

In detail, the main frame 10 has an arc shape having an opened portion so as to surround the pipeline P. For example, the arc shape may have an angle of 200°. In addition, a guide groove 11 is formed in an external surface of the main frame 10 so that the main movement units 21, 22, and 23 may move in a formation direction of the main frame 10, that is, in a circumferential direction of the pipeline P.

The main movement units 21, 22, and 23 are movably installed on the main frame 10, and are movably installed along the length direction of the pipeline P while being in contact with an external circumferential surface of the pipeline P.

In addition, the main movement units 21, 22, and 23 include a center side main movement unit 21, a first end side main movement unit 22, and a second end side main movement unit 23. The center side main movement unit 21, the first end side main movement unit 22, and the second end side main movement unit 23 are spaced apart from one another and are movably installed along the main frame 10 in the circumferential direction of the pipeline P.

In detail, the center side main movement unit 21 is installed in a center portion of the main frame 10, and the first end side main movement unit 22 and the second end side main movement unit 23 are separated from each other with respect to the center side main movement unit 21.

Here, the center side main movement unit 21 and the first and second end side main movement units 22 and 23 are contacted at three points of the external circumferential surface of the pipeline P which are spaced apart at predetermined angles with respect to a center of the pipeline P, thereby firmly supporting the main frame 10 with respect to the pipeline P.

In addition, the center side main movement unit 21 includes a movement bracket 211, a driving unit 212, an extension unit 213, a movement wheel 214, a movement wheel driving unit 215, and an auxiliary wheel 216.

In detail, the movement bracket 211 is connected to the main frame 10, and is slidable along the main frame 10 in the circumferential direction of the pipeline P. The movement bracket 211 may be moved by being guided along the guide groove 11 of the main frame 10.

The driving unit 212 provides a driving force to move the movement bracket 211 with respect to the main frame 10. For example, while being fixed to the main frame 10, a portion of the driving unit 212 is in mesh with the movement bracket 211, thereby moving the movement bracket 211 with respect to the main frame 10 in the circumferential direction of the pipeline P. The driving unit 212 may be a motor that generates a rotational force by using electricity.

While one end of the extension unit 213 is fixed to the movement bracket 211, the extension unit 213 is extended toward the pipeline P. The movement wheel 214 is installed at another end of the extension unit 213. The extension unit 213 is length-variable so that a distance between the movement wheel 214 and the movement bracket 211 may be adjusted according to an external signal.

The movement wheel 214 is rotatably disposed with respect to a rotation axis that crosses the length direction of the pipeline P. That is, the movement wheel 214 is connected to the extension unit 213 so as to move the main movement unit 21 and the pipeline inspecting apparatus 1 in the length direction of the pipeline P. The movement wheel 214 is selectively contacted to the external circumferential surface of the pipeline P.

In addition, the movement wheel driving unit 215 provides a driving force to the movement wheel 214, and may be, for example, a motor that generates a rotational force using electricity.

The auxiliary wheel 216 is mounted adjacent to the movement wheel 214, and is installed to the another end of the extension unit 213, and is able to rotate in the same direction as the movement wheel 214. The auxiliary wheel 216 allows that the pipeline inspecting apparatus 1 stably moves with the movement wheel 214.

Meanwhile, the first end side main movement unit 22 also includes a movement bracket 221, a driving unit 222, an extension unit 223, a movement wheel 224, a movement wheel driving unit 225, and an auxiliary wheel 226.

The movement bracket 221 of the first end side main movement unit 22 has an arc shape that is extended in the same direction as the formation direction of the main frame 10. Also, the extension unit 223 is connected to an end portion of the movement bracket 221 so that the extension unit 223 and the movement wheel 224 are separated away from an end portion of the main frame 10.

In addition, an adjustment groove 227 to which an end side adjusting unit 42 is connected may be formed in the movement bracket 221. A position of the adjusting unit 42 may be adjusted in the adjustment groove 27. The adjustment groove 227 may have, for example, an arc shape.

The structure of the second end side main movement unit 23 is substantially the same as the structure of the first end side main movement unit 22, and thus description thereof will not be provided.

Meanwhile, the auxiliary frame 30 has an arch shape having an opened portion so as to surround the pipeline P. The auxiliary frame 30 is spaced apart to face the main frame 10. The auxiliary frame 30 according to the current embodiment of the present invention has a form corresponding to the main frame 10.

The auxiliary frame adjusting units 41, 42, and 43 connect the auxiliary frame 30 to the main movement units 21, 22, and 23 such that the auxiliary frame 30 is rotatable in the circumferential direction of the pipeline P.

In addition, the auxiliary frame adjusting units 41, 42, and 43 include a center side adjusting unit 41 that is disposed in a center portion of the main frame 10 and a pair of end sides adjusting units 42 and 43 that are separated from each other with respect to the center side main adjusting unit 41. The end side adjusting units 42 and 43 include a first end side adjusting unit 42 and a second end side adjusting unit 43.

One ends of the center side adjusting unit 41 and the first and second end side adjusting units 42 and 43 are connected to the center side main movement unit 21 and the first and second end side main movement units 22 and 23, respectively. Also, another ends of the center side adjusting unit 41 and the first and second end side adjusting units 42 and 43 are connected to the auxiliary frame 30 such that the auxiliary frame 30 is rotatably connected to the main frame 10 in the circumferential direction of the pipeline P.

Meanwhile, the center side adjusting unit 41 includes a first adjustment frame 411, a second adjustment frame 412, a first driving unit 413, and a second driving unit (not shown).

In detail, the first adjustment frame 411 is extended in the length direction of the pipeline P. One end of the first adjustment frame 411 is connected to the movement bracket 211 of the center side main movement unit 21. The first adjustment frame 411 may be connected to the movement bracket 211 via a fixing bracket 414 that is formed at the one end of the first adjustment frame 411.

The second adjustment frame 412 is formed in a direction to cross an extension direction of the first adjustment frame 411. According to the current embodiment of the present invention, the second adjustment frame 412 is extended in a direction that is perpendicular to the extension direction of the first adjustment frame 411. One end of the second adjustment frame 412 is movably connected to the first adjustment frame 411 in the extension direction of the first adjustment frame 411.

The first driving unit 413 provides a driving force to rotate the auxiliary frame 30 with respect to the first adjustment frame 411 and the second adjustment frame 412 in the circumferential direction of the pipeline P.

One end of the first driving unit 413 is movably connected to the second adjustment frame 411 in an extension direction of the second adjustment frame 412. Also, another end of the first driving unit 413 is in mesh with the auxiliary frame 30. Accordingly, the auxiliary frame 30 does not get out of a predetermined movement path formed along the circumferential direction of the pipeline P. That is, detachment of the auxiliary frame 30 from the pipeline inspecting apparatus 1 may be prevented. Also, the pipeline inspecting apparatus 1 may further include a detachment preventing unit for preventing detachment of the auxiliary frame 30.

In addition, the second driving unit provides a driving force that moves the second adjustment frame 412 with respect to the first adjustment frame 411. That is, movement of the second adjustment frame 412 with respect to the first adjustment frame 411 may be performed using the second driving unit.

Also, movement of the first driving unit 413 with respect to the second adjustment frame 412 may be performed by itself. That is, the first driving unit 413 provides a driving force to rotate the auxiliary frame 30 in the circumferential direction of the pipeline P and a driving force for the first driving unit 413 to move with respect to the second adjustment frame 412.

Meanwhile, the first end side adjusting unit 42 and the second end side adjusting unit 43 also include first adjustment frames 421 and 431, second adjustment frames 422 and 432, first driving unit 423 and 433, second driving units (not shown), and a fixing bracket 434. The structures of the first and second end side adjusting units 42 and 43 are substantially the same as the structure of the center side adjusting unit 41, and thus description thereof will not be provided.

That is, the auxiliary frame 30 is connected to the main movement units 21, 22, and 23 via the center side adjusting unit 41 and the first and second end side adjusting units 42 and 43. The center side adjusting unit 41 and the first and second end side adjusting units 42 and 43 adjust relative distances between the auxiliary frame 30 and the main movement units 21, 22, and 23 and relative displacement thereof, thereby adjusting minute angles of the auxiliary frame 30 with respect to the main frame 10.

Accordingly, according to the pipeline inspecting apparatus 1 according to the current embodiment of the present invention, even when the pipeline P has a pipe bend form which is bent at a predetermined angle with respect to the length direction, inspection may be reliably performed by adjusting the minute angle of the auxiliary frame 30.

Meanwhile, the sensor adjusting unit 60 is fixed to the auxiliary frame 30. A sensor (not shown) is installed in the sensor adjusting unit 60 in order to inspect a state of the pipeline P. The sensor adjusting unit 60 is rotatably disposed in a circumferential direction together with the auxiliary frame 30. While the sensor adjusting unit 60 rotates with respect to the pipeline P, the sensor may inspect a state of the external circumferential surface of the pipeline P.

In addition, the sensor adjusting unit 60 includes a first guide rail 61, a sensor movement unit 63, and a second guide rail 62.

One end of the first guide rail 61 is fixed to a center of the auxiliary frame 30, and is extended in a direction perpendicular to the circumferential direction of the pipeline P.

The sensor is installed in the sensor movement unit 63, and is movably installed in an extension direction of the first guide rail 61. The sensor movement unit 63 may include a driving motor generating a driving force.

The guide rail 62 is in mesh at end portion of the sensor movement unit 63

A pair of the pipeline supporting units 51 and 52 may be provided. The pipeline supporting units 51 and 52 include a first pipeline supporting unit 51 and a second pipeline supporting unit 52. One ends of the first pipeline supporting unit 51 and the second pipeline supporting unit 52 are respectively fixed to end portions of the main frame 10, and another ends thereof are selectively contacted to the external circumferential surface of the pipeline P. Accordingly, the main frame 10 may be fixed to the pipeline P via the first and second pipeline supporting units 51 and 52.

Also, the first pipeline supporting unit 51 includes a fixing unit 511, a connection unit 512, and a contact unit 513.

The fixing unit 511 is fixed to an end portion of the main frame 10.

One end of the connection unit 512 is connected to the fixing unit 511 and is extended toward the pipeline P. An extension length of the connection unit 512 is variable.

The contact unit 513 is installed on another end of the connection unit 512, and selectively contacts the external circumferential surface of the pipeline P. The contact unit 513 may have a round shape so as to effectively contact the external circumferential surface of the pipeline P.

Hereinafter, a method of inspecting the pipeline P using the pipeline inspecting apparatus 1 according to the current embodiment of the present invention will be described in detail.

First, the pipeline inspecting apparatus 1 is installed on the pipeline P such that the movement wheels 214, 224, and 234 of the plurality of main movement units 21, 22, and 23 contact the external circumferential surface of the pipeline P. As the three movement wheels 214, 224, and 234 contact the external circumferential surface of the pipeline P at three points and are pressurized, the pipeline inspecting apparatus 1 may be stably installed on the pipeline P.

Also, while the pipeline inspecting apparatus 1 is installed on the pipeline P, the pipeline inspecting apparatus 1 is moved in the length direction of the pipeline P. As the movement wheels 214 contacting the external circumferential surface of the pipeline P rotate, the pipeline inspecting apparatus 1 may be moved in the length direction of the pipeline P.

Also, when the pipeline inspecting apparatus 1 reaches an inspection point of the pipeline P, the auxiliary frame 30 of the pipeline inspecting apparatus 1 is rotated in the circumferential direction of the pipeline P while the main movement units 21, 22, and 23 of the pipeline inspecting apparatus 1 are stopped, thereby inspecting a state of the pipeline P.

The auxiliary frame 30 may be rotated using the center side adjusting unit 41, the first end side adjusting unit 42 and the second end side adjusting unit 43. According to a rotational angle, the auxiliary frame 30 may be detached from one of the first and second end side adjusting units 42 and 43.

In addition, in order to improve inspection reliability by stably fixing the pipeline inspecting apparatus 1 with respect to the pipeline P, the contact unit 513 of the pipeline supporting units 51 and 52 may be contacted to the external circumferential surface of the pipeline P.

While the pipeline inspecting apparatus 1 according to the current embodiment of the present invention is moved in the length direction of the pipeline P, if movement of the pipeline inspecting apparatus 1 is restricted by an obstacle such as a supporting member for supporting the pipeline P, an avoiding operation is performed.

Hereinafter, an operation in which the pipeline inspecting apparatus 1 avoids the obstacle will be described in detail.

Figure 5:
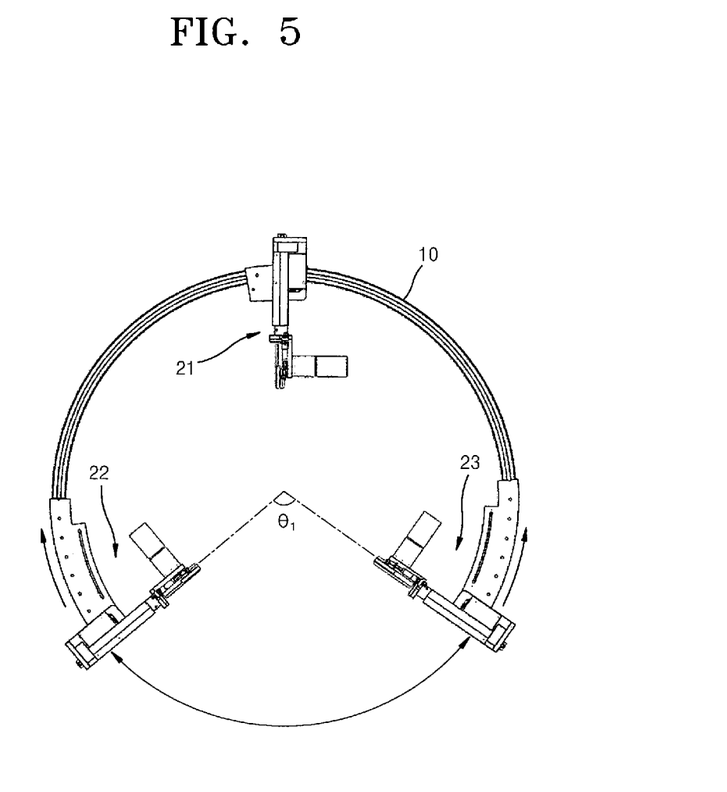
FIGS. 5 and 6 are views illustrating a process in which a pipeline inspecting apparatus avoids an obstacle according to an embodiment of the present invention.
Figure 6:
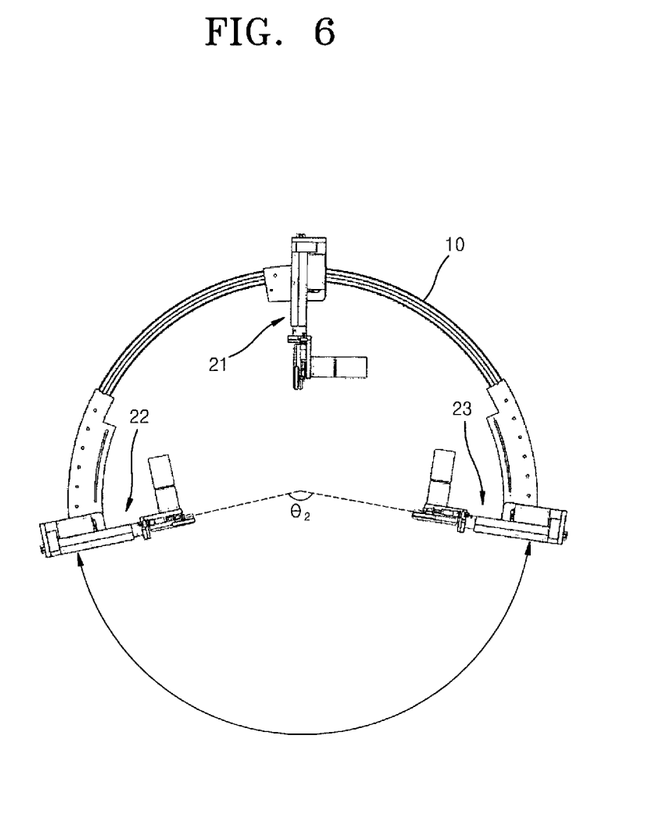

FIGS. 5 and 6 are views illustrating a process in which the pipeline inspecting apparatus avoids an obstacle according to an embodiment of the present invention.

Referring to FIGS. 5 and 6, first, the main frame 10 is fixed to the pipeline P using a pair of the pipeline supporting units 51 and 52 installed at the end portions of the main frame 10.

While the main frame 10 is fixed to the pipeline P, the movement wheels 214, 224, and 234 of the main movement units 21, 22, and 23 contacting the pipeline P are lifted up from the external circumferential surface of the pipeline P, thereby releasing the contact between the movement wheel 214 and the pipeline P.

After lifting up the movement wheels 214, 224, and 234, the main movement units 21, 22, and 23 are moved along the circumferential direction of the pipeline P along the main frame 10.

According to the current embodiment of the present invention, as illustrated in FIGS. 5 and 6, the first end side main movement unit 22 and the second end side main movement unit 23 are moved toward the center side main movement unit 21.

Consequently, an angle $\theta_2$ between the first end side main movement unit 22 and the second end side main movement unit 23 is increased to be greater than an angle $\theta_1$ therebetween before the movement thereof. Thus, a distance between the first end side main movement unit 22 and the second end side main movement unit 23 is increased, thereby providing space for the pipeline inspecting apparatus 1 to avoid the obstacle.

After the main movement units 21, 22, and 23 are moved in the circumferential direction of the pipeline P, the movement wheels 214, 224, and 234 of the main movement units 21, 22, and 23 are contacted to the external circumferential surface of the pipeline P.

Next, fixation of the pipeline supporting units 51 and 52 that fix the main frame 10 with respect to the pipeline P is released.

Accordingly, the pipeline inspecting apparatus 1 may move in the length direction of the pipeline P while space to avoid the obstacle is provided.

According to the current embodiment of the present invention, the pipeline inspecting apparatus may be easily installed on the pipeline, and even when the diameter of the pipeline is varied or the pipeline is formed of a pipe bend inclined at a predetermined angle, inspection of the pipeline may be performed reliably.

Also, as a portion of the main frame of the pipeline inspecting apparatus is opened, an obstacle such as a support of the pipeline may be avoided during movement in the length direction of the pipeline inspecting apparatus.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A pipeline inspecting apparatus moving along an external circumferential surface of a pipeline to inspect the pipeline, comprising:
  a main frame having an arc shape having an opened portion to surround the pipeline;
  a main movement unit that is movably installed on the main frame, wherein the main movement unit is movably installed along a length direction of the pipeline while being in contact with the external circumferential surface of the pipeline;
  an auxiliary frame that has an arc shape having an opened portion to surround the pipeline and is separated from the main frame to face the main frame;
  an auxiliary frame adjusting unit that movably connects the auxiliary frame to the main movement unit in a circumferential direction of the pipeline; and
  a sensor adjusting unit that is fixed to the auxiliary frame, wherein a sensor for inspecting a state of the pipeline is installed.

2. The pipeline inspecting apparatus of claim 1, wherein the main movement unit comprises:
  a center side main movement unit installed in a center portion of the main frame; and
  a pair of end side main movement units that are spaced apart from each other with respect to the center side main movement unit, wherein the end side main movement units are movably installed on the main frame in the circumferential direction of the pipeline,
  wherein the center side main movement unit and the end side main movement units respectively contact three points of the external circumferential surface of the pipeline that are spaced apart at predetermined angles with respect to a center of the pipeline.

3. The pipeline inspecting apparatus of claim 2, wherein the center side main movement unit and the end side main movement units each comprise:
  a movement bracket that is slidably connected along the main frame in the circumferential direction of the pipeline;
  a driving unit that provides a driving force for rotating the movement bracket;
  an extension unit that is extended from the movement bracket toward the pipeline; and
  a movement wheel that is rotatably connected to the extension unit around a rotation axis that crosses a length direction of the pipeline, and selectively contacts the external circumferential surface of the pipeline.

4. The pipeline inspecting apparatus of claim 3, wherein the center side main movement unit and the end side main movement units further comprise an auxiliary wheel that is disposed adjacent to the movement wheel, and is rotatably installed in the same direction as the movement wheel.

5. The pipeline inspecting apparatus of claim 3, wherein the extension unit is length-variable such that a distance between the movement wheel and the movement bracket is adjustable.

6. The pipeline inspecting apparatus of claim 1, wherein the auxiliary frame adjusting unit comprises:
  a center side adjusting unit that is disposed in a center portion of the main frame; and
  a pair of end side adjusting units that are spaced apart from each other with respect to the center side main movement unit,
  wherein one ends of the center side adjusting unit and the end side adjusting units are connected to the main movement unit and another ends of the center side adjusting unit and the end side adjusting units are connected to the auxiliary frame so as to rotatably connect the auxiliary frame with respect to the main frame in the circumferential direction of the pipeline.

7. The pipeline inspecting apparatus of claim 6, wherein the center side main movement unit and the end side main movement units each comprise:
  a first adjustment frame, whose one end is connected to the main movement unit, wherein the first adjustment frame is extended in the length direction of the pipeline;
  a second adjustment frame that is extended in a direction that crosses the direction in which the first adjustment frame is extended, wherein one end of the second adjustment frame is connected to the first adjustment frame, and the second adjustment frame is movable in the extension direction of the first adjustment frame; and
  a first driving unit, whose one end is movably connected to the second adjustment frame in the extension direction of the second adjustment frame, wherein the first driving unit provides a driving force to rotate the auxiliary frame in the circumferential direction of the pipeline.

8. The pipeline inspecting apparatus of claim 7, wherein the center side adjusting unit and the end side adjusting units each further comprise a second driving unit that provides a driving force that moves the second adjustment frame with respect to the first adjustment frame.

9. The pipeline inspecting apparatus of claim 1, wherein the sensor adjusting unit comprises:
   a first guide rail, whose one end is fixed to a center of the auxiliary frame and which extends in a direction perpendicular to the external circumferential surface of the pipeline; and
   a sensor movement unit that is movably installed in the extension direction of the first guide rail, wherein the sensor is installed in the movement unit.

10. The pipeline inspecting apparatus of claim 1, further comprising a pair of pipeline supporting units, wherein one ends of the pipeline supporting units are fixed to the end portions of the main frame and another ends of the pipeline supporting units are selectively contacted to the external circumferential surface of the pipeline so as to fix the main frame with respect to the pipeline.

11. The pipeline inspecting apparatus of claim 10, wherein the pipeline supporting units comprise:
   a fixing unit that is fixed to the end portions of the main frame;
   a connection unit that is extended toward the pipeline while one end of the connection unit is connected to the fixing unit, and an extension length of the connection unit is variable; and
   a contact unit that is installed at another end of the connection unit and selectively contacts the external circumferential surface of the pipeline.

12. A pipeline inspecting method using the pipeline inspecting apparatus of claim 1, the method comprising:
   installing the pipeline inspecting apparatus to a pipeline such that each movement wheel of a plurality of main movement units contacts an external circumferential surface of the pipeline;
   moving the pipeline inspecting apparatus in a length direction of the pipeline; and
   inspecting a state of the pipeline by rotating an auxiliary frame of the pipeline inspecting apparatus in a circumferential direction of the pipeline while the plurality of main movement units of the pipeline inspecting apparatus are stopped.

13. The pipeline inspecting method of claim 12, further comprising avoiding interference due to an obstacle when movement of the pipeline inspecting apparatus is interfered by the obstacle during the moving, by rotating a main frame and the main movement units of the pipeline inspecting apparatus,
   wherein the avoiding comprises:
   fixing the main frame to the pipeline by using a pair of pipeline supporting units installed at end portions of the main frame;
   lifting a movement wheel of the main movement units contacting the pipeline while the main frame is fixed to the pipeline, thereby release the contact between the movement wheel and the pipeline;
   moving the main movement unit along the main frame in a circumferential direction of the pipeline after lifting up the movement wheel;
   contacting the movement wheel of the main movement unit to the external circumferential surface of the pipeline after the main movement units are moved in the circumferential direction of the pipeline; and
   releasing the fixation of the pipeline supporting units that fix the main frame to the pipeline.

* * * * *